(12) United States Patent
Annighoefer et al.

(10) Patent No.: US 7,301,346 B2
(45) Date of Patent: Nov. 27, 2007

(54) HAND LAMP, ESPECIALLY FOR MAGNETIC CRACK DETECTION

(75) Inventors: Rolf Annighoefer, Westhausen (DE); Sigmar Tomaschko, Aalen (DE); Thomas Vetterlein, Offenbach (DE)

(73) Assignee: Illinois Tool Works, Inc., Glenview, IL (US)

( * ) Notice: Subject to any disclaimer, the term of this patent is extended or adjusted under 35 U.S.C. 154(b) by 0 days.

(21) Appl. No.: 10/554,919

(22) PCT Filed: Apr. 29, 2004

(86) PCT No.: PCT/DE2004/000891

§ 371 (c)(1),
(2), (4) Date: Oct. 31, 2002

(87) PCT Pub. No.: WO2004/097385

PCT Pub. Date: Nov. 11, 2004

(65) Prior Publication Data

US 2007/0014195 A1 Jan. 18, 2007

(30) Foreign Application Priority Data

Apr. 30, 2003 (DE) .......................... 203 06 789 U

(51) Int. Cl.
*G01R 31/00* (2006.01)
*G01N 27/84* (2006.01)
*F21L 4/02* (2006.01)
*F21V 29/00* (2006.01)

(52) U.S. Cl. ...................... 324/414; 324/216; 362/184; 362/264

(58) Field of Classification Search ................ 324/216, 324/414, 403; 362/264
See application file for complete search history.

(56) References Cited

U.S. PATENT DOCUMENTS

| | | | | | |
|---|---|---|---|---|---|
| 2,864,996 | A | * | 12/1958 | Linderman | ................... 324/414 |
| 3,825,821 | A | * | 7/1974 | Forster | ....................... 324/216 |
| 5,804,822 | A | * | 9/1998 | Brass et al. | .................. 250/302 |
| 6,644,835 | B2 | * | 11/2003 | Sei et al. | ..................... 362/373 |
| 7,023,232 | B2 | * | 4/2006 | Yano et al. | .................. 324/767 |
| 7,204,606 | B2 | * | 4/2007 | Brass et al. | .................. 362/231 |
| 2002/0093649 | A1 | * | 7/2002 | Brass | ....................... 356/237.1 |
| 2005/0265035 | A1 | * | 12/2005 | Brass et al. | .................. 362/451 |
| 2006/0239005 | A1 | * | 10/2006 | De Godzinsky | ............ 362/276 |
| 2007/0121786 | A1 | * | 5/2007 | Okawa et al. | ............... 378/119 |

FOREIGN PATENT DOCUMENTS

JP 11094804 A * 4/1999

\* cited by examiner

*Primary Examiner*—Anjan Deb
(74) *Attorney, Agent, or Firm*—David S. Safran

(57) ABSTRACT

The invention relates to a manual lamp, especially for optical crack testing according to the magnetic powder testing and dye penetration method. Said manual lamp comprises at least one LED having an emission wavelength located in the UVA range as an illuminating means.

11 Claims, 1 Drawing Sheet

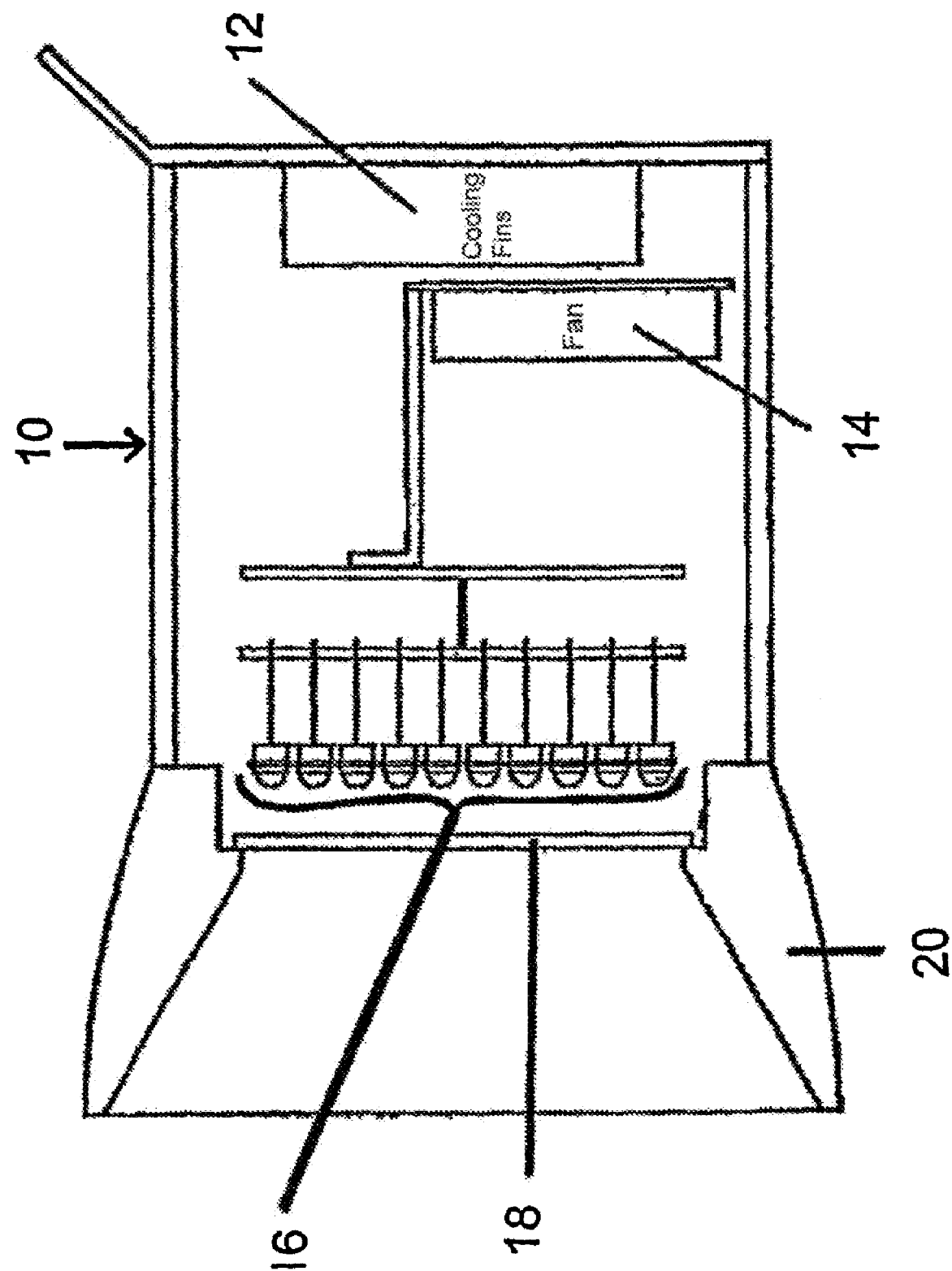

HAND LAMP, ESPECIALLY FOR MAGNETIC CRACK DETECTION

BACKGROUND OF THE INVENTION

1. Filed of Invention

The invention relates to a hand lamp especially for magnetic crack detection and using the dye penetration process.

2. Description of Related Art

Hand lamps for crack detection are known. They are used for flaw detection in optical crack detection using the dye penetration process and magnetic crack detection to reveal the concentration of fluorescent particles in cracks in a higher concentration of dye particles by their fluorescence and thus for determining cracks. As the technical background, German Patent Application DE 19639020 A1 is mentioned, in which a generic dye penetration process is explained, the use of the hand lamp in accordance with the invention in no way being limited to this application. Typical applications of hand lamps are especially the checking of poorly accessible cavities like the inside walls of pipes, surfaces which are not illuminated in incident light—in general, areas which can be poorly reached, or rapid checking of parts on site. In the past UV hand lamps were used in which a UV burner emitted the necessary UV radiation—optionally with a filter connected on the input side. These UV burners unfortunately did not have a long service life.

Furthermore, the emission spectrum dropped to longer wavelength ranges within a short time; this led to these lamps no longer performing the task of exciting fluorescence in a certain UV range to a sufficient degree. Furthermore, the known UV sources were unwieldy and had large dimensions—this was often caused by the necessity of connecting a series reactor upstream in fluorescent tubes. In addition, there was a relatively high weight; this likewise made fine motor handling difficult.

Therefore it is a hand lamp here in which in the known manner workpieces for dye penetration testing are treated with a testing agent which has dyes, with concentration of the dyes on surface flaws, and are evaluated under illumination by an illumination means such as UV lamps for fluorescent dyes, but also lasers or other lamps with the correspondingly absorbing dyes.

Therefore, in the known manner, workpieces for dye penetration testing are prepared by cleaning them, optionally pickling and drying them, spraying with a testing agent which has dyes, especially also fluorescent dyes, with concentration of the dyes on the surface flaws, especially cracks, then wiping or scraping off the excess dye-containing testing agents, treating the workpiece which has been treated in this way optionally with a developer and then viewing it under UV light after a predetermined development time and evaluating it.

Dye penetration studies and magnetic powder tests can be carried out by operators and can be evaluated by appearance—but it is also possible to automatically evaluate them by special optical processes. The applicant has already proposed dye penetration testing processes of this type, in addition to the pertinent device.

Accordingly, the object of the invention is to avoid the disadvantages of hand lamps which emit in the UV range, especially for the dye penetration process and the magnetic powder testing process.

SUMMARY OF THE INVENTION

This object is achieved in accordance with the invention by a hand lamp, especially for magnetic crack detection, which has at least one LED with an emission wavelength in the UVA range as an illuminant. Advantageous developments result from the dependent claims.

Light generation in a LED hand lamp takes place in the LED directly by changing the path of the electrons in a semiconductor crystal. Based on this fact, light radiation only occurs in the wavelength range which corresponds to the quanta emitted when the path of the electrons changes. In contrast, thermal radiators such as conventional UV lamps, emit continuously in a very wide spectral range, which is unnecessary or harmful for crack detection and must be filtered out in the known UV lamps. Especially UVB and UVC radiation which is toxic and which occurs in classic UV lamps can be eliminated by the LED in accordance with the invention as the illuminant. The formation of harmful radiation in the shortwave UV range which is damaging to the ocular fundus and dangerous to the skin of the operator, since this radiation causes "sunburn" or radiation damage, is thus eliminated.

Because at this point LEDs which emit specifically only in one wavelength range are being used, much less energy is required to produce the light quanta of wavelengths which are required for detection, and heating of the lamp is avoided. Another advantage of LEDs is their long service life; in contrast to conventional UV radiators, it is many times longer.

LEDs do not exhibit ageing in the emission spectrum—in contrast to thermal illuminants, by which a uniform quality of crack detection is enabled. LEDs do not require a warm-up phase, i.e. emission is for the most part constant—in contrast to conventional hand lamps for this range. Nor do they require a warm-up phase so that the complete spectrum is immediately available after the lamp is turned on—in contrast to thermal UV lamps which first require a stable operating temperature to build up a stable spectrum.

Since LEDs require much less energy than other illuminants, the hand lamp in accordance with the invention can also have a portable energy source such as a battery or a storage cell and thus can be used independently of a power source, as in the testing of workpieces at construction sites, etc. A DC voltage of 12 or 24 volts is quite sufficient for operation. It lies in the range of so-called extra-low safety voltage; this is important for operation in a wet environment and for splashing water and in tanks. Power supply with a motor vehicle battery is possible in very inaccessible articles—for example, in the testing of pipelines.

Another advantage of LEDs is their long service life which far exceeds conventional UV lamps. The service life of LEDs is more than 50,000 hours, i.e., more than 5 years of uninterrupted operation (the service life of a LED is defined as a drop of the light intensity to 50% at the rated wattage). Finally, LEDs are not vibration-sensitive like gas discharge lamps which easily break when the housing is struck or the lamp is allowed to drop, while LEDs are relatively insensitive to these effects.

It is especially preferred that the hand lamp in addition to the LED has at least one other illuminant which emits in the 400-800 nm range, and the two illuminants can be turned on and off separately from one another. In this way the operator has a positioning lamp which allows him to direct the UVA radiation which is invisible to the human eye. Preferably this illuminant can likewise be less energy-consuming, such as another LED which emits in the visible range or a LASER.

Furthermore, the hand lamp can also have a white light lamp which enables the operator to inspect the test field in general.

Typical outside dimensions of a hand lamp in accordance with the invention are roughly 100×100×140 mm (without a handle) and their weight is 1 kg.

Due to the fact that the LEDs require only low operating voltages, the hand lamp can be much more reliably safeguarded than those of the prior art which [require] extremely complex safety measures for the high voltage which is necessary for ignition of a fluorescent tube via a reactor.

It is important to thermally stabilize the LEDs during operation—at elevated temperatures the intensity of the LEDs decreases. Accordingly, the power supply of the LED must be controlled such that it runs as much as possible not at the maximum wattage, so that the LED can be prevented from becoming hot. The intensity of a LED is a function of the power consumption, therefore the supply current of the LEDs must be controlled such that they run in a middle wattage range in order to obtain optimum light yield. Furthermore, to prevent overheating there is preferably a cooling means, such as ventilation slits, fans, and the like.

The control can induce either continuous displays or displays only in an emergency, if monitoring means, such as the temperature sensor, UV sensor, or voltmeter have values outside of a standard range.

Thus, among others the following advantages are achieved by the hand lamp in accordance with the invention:
Prevention of the formation of UVB and UVC
Battery operation at extra-low safety voltage
Immediate readiness for operating after being turned on
Small dimensions
Long service life of the illuminant—less maintenance
Microprocessor monitoring
Insensitivity to vibration One preferred embodiment is detailed below using the drawing to which the invention is in no way limited.

BRIEF DESCRIPTION OF THE DRAWINGS

The sole FIGURE shows a cross section through a schematically shown hand lamp.

DETAILED DESCRIPTION OF THE INVENTION

As is apparent from the FIG., the hand lamp has a housing 10 with a rib cooling body 12 and a fan 14. Both are used for cooling the LEDs 16 which are located in a radiation field, and as shown, are mounted to a common plate structure the fan within a lamp housing with the rib cooling body being mounted to an end wall of the lamp housing. In front of the radiation field there is a protective pane 18 and a frame for the pane which protects the latter. Cool air from the area of the rib cooling body is routed in the direction of the LED and in the lamp by operation of the fan and thus cooling and prevention of local heating are achieved.

Preferably the housing is splash-proof, therefore leak-proof, and satisfies standard IP65. The lamp furthermore has a control such as a microprocessor which monitors by way of temperature sensors whether a threshold temperature has been exceeded and accordingly controls the power supply to the LEDs. In this way it can be ensured that heat generation can be stabilized. Furthermore, there can be at least one UV sensor in order to check the emission of the LED, and general voltage monitoring. The signals of these measurement means are processed by the control, and optionally displays such as warning lamps, display instruments, etc. are triggered, by which the operator is warned if a battery failure is pending or the power supply is not sufficient. The operator is also warned against overheating of the lamp or against faults of the UV source.

Although the invention has been explained using preferred embodiments, modifications of it are familiar to one skilled in the art and likewise fall within the protective scope of the claims, so that the invention is in no way limited to the exemplary embodiments.

What is claimed is:

1. Hand lamp for magnetic crack detection using magnetic powder testing and the dye penetration process, comprising:
a plurality of LEDs with an emission wavelength in the UVA range as the illuminant,
cooling means, and
at least one other illuminant which emits white light in the a range visible to the human eye,
wherein the illuminants can be turned on and off separately from one another,
wherein said cooling means comprises a rib cooling body and a fan, and
wherein the LEDs and the fan are mounted to a common plate structure within a lamp housing and the rib cooling body is mounted to an end wall of the lamp housing.

2. Hand lamp as claimed in claim 1, further comprising a portable power source.

3. Hand lamp as claimed in claim 2, wherein said power source is one of a battery and power cell.

4. Hand lamp as claimed in claim 1, wherein outside dimensions of the lamp are roughly 100×100×140 mm.

5. Hand lamp as claimed in claim 1, further comprising a control which controls the current supply of the LEDs according to stipulated quantities and from received measurement signals.

6. Hand lamp as claimed in claim 1, further comprising displays for malfunctions.

7. Hand lamp as claimed in claim 6, wherein said displays are display lamps or instruments.

8. Hand lamp as claimed in claim 1, wherein the housing is splash-proof.

9. Hand lamp as claimed in claim 1, wherein the lamp weighs roughly 1000 g.

10. Hand lamp as claimed in claim 1, further comprising a control which controls the current supply of the LEDs according to stipulated quantities and from received measurement signals representative of lamp temperature.

11. Hand lamp as claimed in claim 1, further comprising a control which controls the current supply of the LEDs according to stipulated quantities and from received measurement signals representative of lamp intensity.

* * * * *